United States Patent
Hwang et al.

(10) Patent No.: US 8,540,703 B2
(45) Date of Patent: *Sep. 24, 2013

(54) METHODS FOR TREATING SKIN CONDITIONS USING LASER

(75) Inventors: Hae Lyung Hwang, Gyeonggi-do (KR); Sung Huan Gong, Seoul (KR); Jing Mei Li, Gyeonggi-do (KR)

(73) Assignee: Lutronic Corporation, Gyeonggi-Do (KR)

( * ) Notice: Subject to any disclaimer, the term of this patent is extended or adjusted under 35 U.S.C. 154(b) by 150 days.

This patent is subject to a terminal disclaimer.

(21) Appl. No.: 13/279,888

(22) Filed: Oct. 24, 2011

(65) Prior Publication Data

US 2012/0041522 A1    Feb. 16, 2012

Related U.S. Application Data

(63) Continuation-in-part of application No. 12/158,350, filed as application No. PCT/KR2006/002043 on May 29, 2006, now Pat. No. 8,048,064.

(30) Foreign Application Priority Data

Dec. 23, 2005  (KR) .......................... 10-2005-0128505

(51) Int. Cl.
*A61B 18/20*    (2006.01)

(52) U.S. Cl.
USPC ............................................................ 606/9

(58) Field of Classification Search
USPC .......................................... 606/4, 9; 128/898
See application file for complete search history.

(56) References Cited

U.S. PATENT DOCUMENTS

| | | |
|---|---|---|
| 5,112,328 A | 5/1992 | Taboada et al. |
| 5,312,396 A | 5/1994 | Feld et al. |
| 5,662,590 A | 9/1997 | de la Torre et al. |
| 5,707,401 A | 1/1998 | Talmore |
| 5,766,214 A | 6/1998 | Mehl, Sr. et al. |
| 5,843,071 A | 12/1998 | Bath |
| 5,873,875 A | 2/1999 | Altshuler |
| 5,885,211 A | 3/1999 | Eppstein et al. |
| 5,919,186 A | 7/1999 | Bath |
| 5,984,916 A | 11/1999 | Lai |
| 6,063,108 A | 5/2000 | Salansky et al. |
| 6,096,031 A | 8/2000 | Mitchell et al. |
| 6,149,671 A | 11/2000 | Nordquist et al. |
| 6,162,211 A * | 12/2000 | Tankovich et al. ................ 606/9 |

(Continued)

FOREIGN PATENT DOCUMENTS

| | | |
|---|---|---|
| JP | 6190071 A | 7/1994 |
| JP | 2003300684 | 10/2003 |

(Continued)

*Primary Examiner* — Bill Thomson
*Assistant Examiner* — Jeffrey Lipitz
(74) *Attorney, Agent, or Firm* — Pepper Hamilton LLP (57) ABSTRACT

Methods of treating a portion of skin are disclosed. A carbon lotion is applied to a portion of skin comprising one or more enlarged pores or one or more indicators of aging. The carbon lotion is allowed to remain on the portion of skin for a period of time, and, upon expiration of the period of time, excess carbon lotion is removed from the portion of skin. The portion of skin is irradiated with one or more first laser pulses and one or more second laser pulses. A laser producing the first and second laser pulses has an oscillation wavelength of 1064 nm.

19 Claims, 8 Drawing Sheets

(56) References Cited

U.S. PATENT DOCUMENTS

| | | |
|---|---|---|
| 6,200,309 B1 | 3/2001 | Rice et al. |
| 6,242,477 B1 | 6/2001 | Okamoto et al. |
| 6,267,755 B1 | 7/2001 | Clementi et al. |
| 6,277,111 B1 | 8/2001 | Clement et al. |
| 6,379,376 B1 | 4/2002 | Lubart |
| 6,387,089 B1 | 5/2002 | Kreindel et al. |
| 6,494,900 B1 | 12/2002 | Salansky et al. |
| 6,524,329 B1 | 2/2003 | Benedict |
| 6,530,915 B1 | 3/2003 | Eppstein et al. |
| 6,595,986 B2 | 7/2003 | Almeida |
| 6,605,080 B1 | 8/2003 | Altshuler et al. |
| 6,607,523 B1 | 8/2003 | Asah et al. |
| 6,613,040 B2 | 9/2003 | Tankovich et al. |
| 6,676,655 B2 | 1/2004 | McDaniel |
| 6,685,730 B2 | 2/2004 | West et al. |
| 6,770,069 B1 | 8/2004 | Hobart et al. |
| 6,786,899 B1 | 9/2004 | Lai |
| 6,936,044 B2 | 8/2005 | McDaniel |
| 6,962,584 B1 | 11/2005 | Stone et al. |
| 6,997,923 B2 | 2/2006 | Anderson et al. |
| 7,041,093 B2 | 5/2006 | Toftkjaer |
| 7,097,656 B1 | 8/2006 | Akopov et al. |
| 7,101,384 B2 | 9/2006 | Benedict |
| 7,108,692 B2 | 9/2006 | Frenz et al. |
| 7,160,289 B2 | 1/2007 | Cohen |
| 7,282,060 B2 | 10/2007 | DeBenedictis et al. |
| 7,283,576 B2 | 10/2007 | Krupke |
| 7,306,620 B2 | 12/2007 | Cumbie |
| 7,309,335 B2 | 12/2007 | Altshuler et al. |
| 7,329,252 B1 | 2/2008 | Yamazaki et al. |
| 7,331,953 B2 | 2/2008 | Manstein et al. |
| 7,351,241 B2 | 4/2008 | Bendett et al. |
| 7,351,252 B2 | 4/2008 | Altshuler et al. |
| 7,353,829 B1 | 4/2008 | Wachter et al. |
| 7,354,448 B2 | 4/2008 | Altshuler et al. |
| 2001/0001118 A1 | 5/2001 | Asah et al. |
| 2001/0050083 A1 | 12/2001 | Marchitto et al. |
| 2002/0019624 A1 | 2/2002 | Clement et al. |
| 2002/0103482 A1 | 8/2002 | Scholler et al. |
| 2002/0107509 A1 | 8/2002 | Neuberger et al. |
| 2002/0161357 A1 | 10/2002 | Anderson et al. |
| 2003/0004556 A1 | 1/2003 | McDaniel |
| 2003/0023283 A1 | 1/2003 | McDaniel |
| 2003/0216719 A1 | 11/2003 | Debenedictis et al. |
| 2004/0093042 A1 | 5/2004 | Altshuler et al. |
| 2004/0162596 A1 | 8/2004 | Altshuler et al. |
| 2004/0167500 A1 | 8/2004 | Weckwerth et al. |
| 2004/0199152 A1 | 10/2004 | Key |
| 2004/0199223 A1 | 10/2004 | Anderson et al. |
| 2004/0225339 A1 | 11/2004 | Yaroslavsky et al. |
| 2004/0230258 A1 | 11/2004 | Altshuler et al. |
| 2004/0243111 A1 | 12/2004 | Bendett et al. |
| 2005/0004632 A1 | 1/2005 | Benedict |
| 2005/0015123 A1 | 1/2005 | Paithankar |
| 2005/0049582 A1 | 3/2005 | DeBenedictis et al. |
| 2005/0049658 A1 | 3/2005 | Connors |
| 2005/0119642 A1 | 6/2005 | Grecu et al. |
| 2005/0154380 A1 | 7/2005 | DeBenedictis et al. |
| 2005/0154381 A1 | 7/2005 | Altshuler et al. |
| 2005/0203495 A1 | 9/2005 | Malak |
| 2005/0215987 A1 | 9/2005 | Slatkine |
| 2005/0222555 A1 | 10/2005 | Manstein et al. |
| 2005/0251231 A1 | 11/2005 | Goldberg |
| 2006/0020309 A1 | 1/2006 | Altshuler et al. |
| 2006/0079947 A1 | 4/2006 | Tankovich et al. |
| 2006/0095095 A1 | 5/2006 | Cao |
| 2006/0095096 A1 | 5/2006 | DeBenedictis et al. |
| 2006/0189967 A1 | 8/2006 | Masotti et al. |
| 2006/0217787 A1 | 9/2006 | Olson et al. |
| 2006/0253178 A1 | 11/2006 | Masotti |
| 2006/0259102 A1 | 11/2006 | Slatkine |
| 2007/0005120 A1 | 1/2007 | Villacampa et al. |
| 2007/0027441 A1 | 2/2007 | Almeida |
| 2007/0032847 A1 | 2/2007 | Weckwerth et al. |
| 2007/0073367 A1 | 3/2007 | Jones et al. |
| 2007/0078500 A1 | 4/2007 | Ryan et al. |
| 2007/0123844 A1 | 5/2007 | Henry |
| 2007/0198068 A1 | 8/2007 | Chan et al. |
| 2007/0219601 A1 | 9/2007 | Neuberger |
| 2007/0260229 A1 | 11/2007 | Navarro et al. |
| 2008/0015554 A1 | 1/2008 | Cole et al. |
| 2008/0015556 A1 | 1/2008 | Chan et al. |
| 2008/0015557 A1 | 1/2008 | Chan et al. |
| 2008/0033516 A1 | 2/2008 | Altshuler et al. |
| 2008/0045933 A1 | 2/2008 | Perl |
| 2008/0058783 A1 | 3/2008 | Altshuler et al. |
| 2008/0058784 A1 | 3/2008 | Manstein et al. |
| 2008/0058904 A1 | 3/2008 | Hillis et al. |
| 2008/0091179 A1 | 4/2008 | Durkin et al. |
| 2008/0147052 A1 | 6/2008 | Bendett et al. |
| 2008/0154344 A1 | 6/2008 | Trusty et al. |
| 2008/0183250 A1 | 7/2008 | Tanojo et al. |
| 2008/0208178 A1 | 8/2008 | DeBenedictis et al. |
| 2008/0208179 A1 | 8/2008 | Chan et al. |
| 2008/0215040 A1 | 9/2008 | Paithankar et al. |
| 2008/0234786 A1 | 9/2008 | Cumbie |
| 2008/0262577 A1 | 10/2008 | Altshuler et al. |
| 2009/0146086 A1 | 6/2009 | Manstein |

FOREIGN PATENT DOCUMENTS

| | | |
|---|---|---|
| JP | 2003310639 | 11/2003 |
| JP | 2005034609 A | 2/2005 |
| KR | 2005051095 A | 6/2005 |
| KR | 200408926 Y1 | 2/2006 |
| WO | WO 03/028807 A1 | 4/2003 |
| WO | WO 2004/037068 A2 | 5/2004 |

* cited by examiner

Irradiate a portion of epidermis with laser
pulses
1100

METHODS FOR TREATING SKIN CONDITIONS USING LASER

CROSS REFERENCE TO RELATED APPLICATIONS

This application is a continuation-in-part of and claims priority to pending U.S. patent application Ser. No. 12/158,350 to Hwang et al., entitled "Method of Curing Inflammatory Acne by Using Carbon Lotion and Pulsed Laser" filed Jun. 20, 2008, which claims priority to International Application No. PCT/KR2006/002043 filed May 29, 2006, which claims priority to Korean Patent Application No. 10-2005-0128505 filed Dec. 23, 2005, each of which is incorporated herein by reference in its entirety.

BACKGROUND

The present invention relates to an acne curing method, and more particularly to a method of curing inflammatory acne by applying a carbon lotion onto a face covered with the acne, irradiating the applied carbon lotion with a laser pulse having a pulse width of about 1 microsecond to about 1000 microseconds, and irradiating the applied carbon lotion with a laser pulse having a pulse width of about 1 nanosecond to about 1000 nanoseconds to sterilize acne bacilli and open skin pores clogged with sebum, thereby entirely treating the inflammatory acne.

It is known that the onset of acne is generally caused by the following four reasons: 1) excessive production of sebum; 2) excessive cell division of follicular epithelium and thus blocking of pores; 3) production of inflammation due to proliferation of *Propionibacterium* acne (*P. acne*) and generation of prefatty acid; and 4) inflammation of follicle and its surrounding area. A major factor affecting the pathogeny mechanism comprises climate or weather, season, modification of gene or hormone, skin wastes, and others.

The onset causes of the acne will be described in detail with reference to the accompanying drawings.

Figure 1:
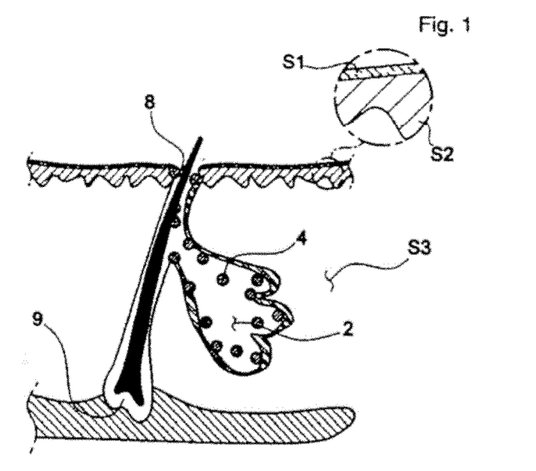
FIG. 1 is a cross-sectional view schematically illustrating a surrounding area of a pore.
Figure 2:
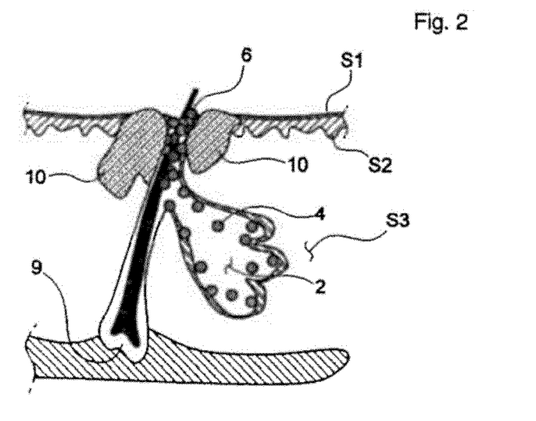
FIG. 2 illustrates an exemplary cross-sectional view schematically illustrating inflammatory acne produced around a pore according to an embodiment.

FIG. 1 is a cross-sectional view schematically illustrating the surrounding area of a pore, and FIG. 2 is a cross-sectional view schematically illustrating inflammatory acne developed around the pore.

Referring to FIGS. 1 and 2, if a sebum 4 is excessively secreted from a sebum gland 2, the sebum 4 is not smoothly discharged from the sebum gland 2, and thus is accumulated in a pore 8. The prefatty acid generated by *Propionibacterium* acne which is proliferated in the pore 8 stimulates the skin around the pore, which can cause inflammation in the wall of a hair follicle and an area around the pore.

With the inflammation, a stratum corneum 51 is abnormally proliferated around the pore 8, and edema caused by the inflammation 10 blocks the pore 8 to further obstruct the smooth discharge of the sebum. Hence, symptoms of acne are developed on the skin. In the drawings, reference numeral S2 denotes an epidermal layer, S3 denotes a dermal layer, and 9 denotes a hair root.

The acne treatment generally takes aim at one or some of four pathogeny mechanisms as described above.

The acne developed by the above reasons is generally cured by the following conventional methods:

1) a method of dosing a patient with drugs such as antibiotics, retinoids, or steroid;
2) a method of using an external application; and
3) a surgical method such as comedo extraction, chemical peeling, or the like.

However, the conventional methods have a limited effect, and give rise to several side effects.

In particular, in case of the chemical peeling in which a chemical drug is applied onto the epidermis to peel off the epidermal layer, the clogged pores are opened to allow the sebum to be smoothly discharged, and the inflamed tissues are eliminated from the skin. However, experienced operators are required, and it is not possible to precisely control a penetrated depth when the drugs are applied, thereby possibly giving rise to side effects, for example, scar or hyper-pigmentation caused by excessive peeling of the epidermal layer. Although a laser having a wavelength of about 400 nm or intense pulsed light is used to cure the acne, because it cannot open the clogged pores, a desired curing effect is not expected. Any method cannot effectively treat the acne to date.

SUMMARY

Therefore, the present invention has been made to solve the above-mentioned problems occurring in the prior art, and an object of the present invention is to provide a method of curing inflammatory acne by using a carbon lotion and a pulsed laser, in which the carbon lotion applied onto a skin is irradiated with a first laser pulse having a relatively long pulse length (i.e., microsecond), so that stratum corneum is separated from an epidermal layer of the skin so as to be easily removed from the epidermal layer, the stratum corneum is eliminated by the reaction of thermal effect, and the epidermal layer and a dermal layer are stimulated to activate generation or reorganization of cells such as collagen and thus further accelerate regeneration of the skin.

Another object of the present invention is to provide a method of curing inflammatory acne by using a carbon lotion and a pulsed laser, in which the carbon lotion applied onto a skin is irradiated with a second laser pulse having a relatively short pulse length (i.e., about 1 nanosecond to about 1000 nanoseconds), so that carbon powders existed in pores are burst out to eliminate a stratum corneum which is already separated by a first laser pulse and to open the pores and passages of the pores clogged by sebum, bacteria, keratin, or the like, through which old sebum, debris of keratin, and others are cleanly removed from the pores.

Further another object of the present invention is to provide a method of curing inflammatory acne by using a carbon lotion and a pulsed laser, in which the carbon lotion applied onto a skin is irradiated with a first laser pulse having a relatively long pulse length (i.e., about 1 microsecond to about 1000 microseconds) and a second laser pulse having a relatively short pulse length (i.e., about 1 nanosecond to about 1000 nanoseconds), thereby sterilizing acne bacilli such as *Propionibacterium* acne and thus eliminating the onset causes of acne.

In order to accomplish the above-mentioned objects, there is provided a method of curing inflammatory acne by using a carbon lotion and a pulsed laser, the method comprising the steps of: applying the carbon lotion onto epidermis to be cured and pores; and irradiating the carbon lotion with a laser pulse to heat and burst the applied carbon lotion.

The irradiating step comprises irradiating the applied carbon lotion with a first laser pulse having a first pulse width to heat the carbon lotion, and irradiating the applied carbon lotion with a second laser pulse having a second pulse width shorter than the first pulse width to burst the carbon lotion in the pore, after the first laser pulse is irradiated.

According to the present invention, the method of curing the inflammatory acne by using the carbon lotion and the pulsed laser has the following effects.

1) The carbon lotion applied onto the epidermis is irradiated with the first laser pulse having a relatively long pulse length (i.e., about 1 microsecond to about 1000 microseconds) and the second laser pulse having a relatively short pulse length (i.e., about 1 nanosecond to about 1000 nanoseconds), in order to simply and effectively cure the inflammatory acne.

2) The carbon lotion applied onto the epidermis is irradiated with the first laser pulse having a relatively long pulse length (i.e., about 1 microsecond to about 1000 microseconds), so that the stratum corneum is evenly eliminated by the heat generated from the carbon lotion, and the epidermal layer and the dermal layer are stimulated.

By stimulating the epidermal layer and the dermal layer, the generation or reorganization of cells such as collagen is activated, and thus the regeneration of the skin cells is further accelerated.

3) Through the uniform regeneration of the dermal cells, the wound is quickly closed, and it can prevent the scar due to the acne.

4) The carbon lotion applied onto the epidermis is irradiated with the second laser pulse having a relatively short pulse length (i.e., about 1 nanosecond to about 1000 nanoseconds), in order to burst out the carbon powders in the pore and thus eliminate the stratum corneum and open the pore.

Through the open of the pore, the old sebum, the debris of keratin, and others are cleanly removed from the pore, so that the passage of the pore clogged by the sebum, the bacteria, the keratin, and others is completely opened.

Since the passage of the pore is completely opened, the secretion of the sebum gland can be adjusted.

5) Since the carbon lotion applied onto the epidermis is irradiated with the first laser pulse having a relatively long pulse length (i.e., about 1 microsecond to about 1000 microseconds) and the second laser pulse having a relatively short pulse length (i.e., about 1 nanosecond to about 1000 nanoseconds), acne bacilli such as *Propionibacterium* acne are sterilized to eliminate the onset causes of acne.

6) According to the above effects, proper prognosis is obtained in the process of curing the acne.

In an embodiment, a method of treating a portion of skin may include applying a carbon lotion to a portion of skin comprising one or more enlarged pores, allowing the carbon lotion to remain on the portion of skin for a period of time, upon expiration of the period of time, removing excess carbon lotion from the portion of skin, irradiating the portion of skin with one or more first laser pulses, and irradiating the portion of skin with one or more second laser pulses, wherein a laser producing the first and second laser pulses has an oscillation wavelength of 1064 nm.

In an embodiment, a method of treating a portion of skin may include applying a carbon lotion to a portion of skin comprising one or more indicators of aging, allowing the carbon lotion to remain on the portion of skin for a period of time, upon expiration of the period of time, removing excess carbon lotion from the portion of skin, irradiating the portion of skin with one or more first laser pulses, and irradiating the portion of skin with one or more second laser pulses, wherein a laser producing the first and second laser pulses has an oscillation wavelength of 1064 nm.

In an embodiment, a method of treating a portion of skin comprising one or more indicators of aging may include irradiating the portion of skin with one or more laser pulses that are generated by a 1064 nm Nd:YAG laser, wherein the one or more laser pulses each have a pulse width in a range of about 5 ns to about 50 ns.

In an embodiment, a method of treating a portion of skin may include irradiating a portion of skin with one or more first laser pulses that are generated by a 1064 nm Nd:YAG laser, wherein the one or more first laser pulses each have a pulse width in a range of about 300 µs, and irradiating the portion of skin with one or more second laser pulses that are generated by a 1064 nm Nd:YAG laser operating in Q-switched mode, wherein the one or more second laser pulses each have a pulse width in a range of about 5 ns to about 50 ns.

DETAILED DESCRIPTION

Figure 3:
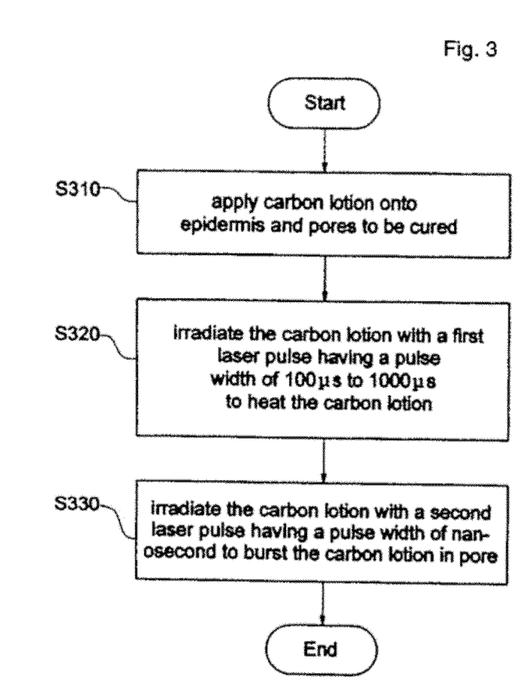
FIG. 3 illustrates an exemplary method of curing inflammatory acne by using a carbon lotion and a pulsed laser according to an embodiment.
Figure 4:
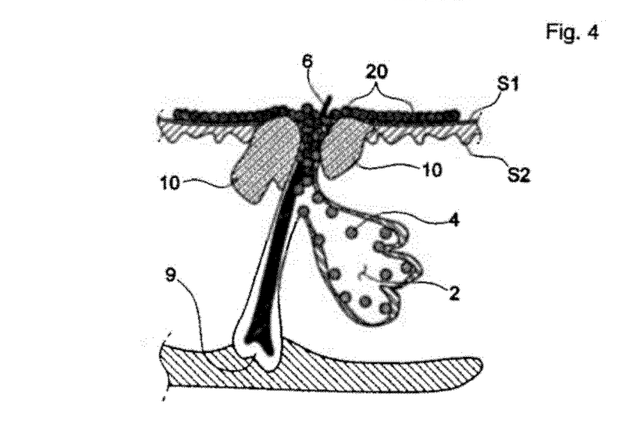
FIG. 4 illustrates an exemplary cross-sectional view schematically illustrating the epidermis applied with a carbon lotion according to an embodiment.

FIG. 3 is a flow diagram explaining a method of curing inflammatory acne by using a carbon lotion and a pulsed laser according to an embodiment, and FIG. 4 is a cross-sectional view schematically illustrating the epidermis applied with the carbon lotion.

In an embodiment, after the epidermis of a skin to be treated is clearly cleaned, a carbon lotion 20 (hereinafter referred to as carbon powders, since the carbon lotion consists of powders) is evenly applied onto the epidermis and pores 8 (step S310), as shown in FIGS. 3 and 4.

The applied thin carbon lotion 20 is evenly irradiated with a first laser pulse L1 having a pulse width of between about 100 µs to 1000 µs by using a pulsed Nd:YAG laser (not shown) (oscillation wavelength: 1064 nm) (step S320). The reason why the carbon lotion 20 is irradiated with the relatively long pulse is that the laser energy is transferred to the carbon lotion to emit heat.

The first laser pulse L1 has a pulse length similar to a pumping time of a lamp (not shown) of the Nd:YAG laser.

The reason which the carbon lotion 20 is used as an igniter is that the carbon lotion absorbs the light having the 1064 nm wavelength which is the oscillation wavelength of the Nd:YAG laser.

Figure 5:
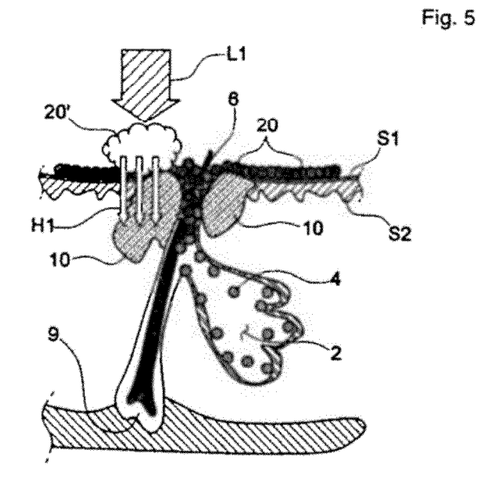
FIG. 5 illustrates a conceptual view of irradiating an exemplary laser pulse onto a carbon lotion according to an embodiment.

When the carbon lotion 20 is irradiated with the first laser to absorb the energy, the heat is generated from the carbon lotion 20, and then the carbon lotion starts to burn. The burning state of the carbon lotion 20 is designated by reference numeral 20 in FIG. 5 which is a conceptual view explaining the case the first laser pulse is irradiated onto the carbon lotion.

Figure 6:
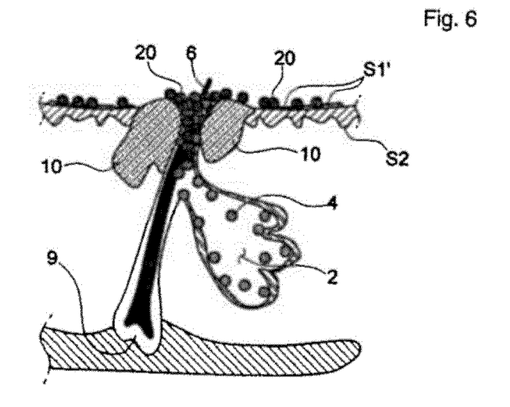
FIG. 6 illustrates exemplary carbon powders left after a first laser pulse is irradiated according to an embodiment.

A stratum corneum S1 is separated from an epidermis by the heat H1 generated from the carbon lotion 20, and simultaneously, an epidermal layer S2 and a dermal layer S3 are stimulated to activate generation or reorganization of cells such as collagen and thus further accelerate regeneration of the skin. In FIG. 6 which is a view illustrating the carbon powders left after the irradiation of the first laser pulse, the stratum corneum which is partially left on the stratum corneum after it is mostly removed is indicated by reference numeral S1'.

Also, burning of the carbon lotion causes *Propionibacterium* acne to be sterilized. As a result, the inflammation 10 developed around the pore by the *Propionibacterium* acne is cured.

The carbon lotion 20 applied onto the epidermis is mostly removed by the first laser pulse L1, but the carbon powders penetrated into the pore 8 are left as it is.

Figure 7:
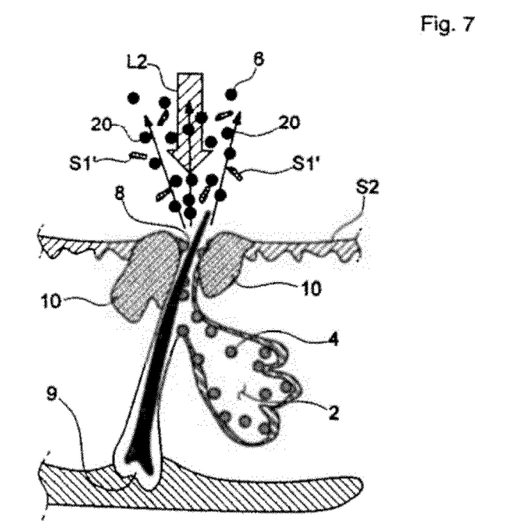
FIG. 7 illustrates a conceptual view of irradiating a second laser pulse onto a carbon lotion according to an embodiment.

FIG. 7 is a conceptual view explaining the case the second laser pulse is irradiated onto the carbon lotion.

After the acne has been treated by the first laser pulse, as shown in FIG. 7, the remaining carbon lotion 20 is irradiated by the second laser pulse L2 from the Nd:YAG laser (not shown) (S330). The second laser pulse L2 is a pulse wave having a pulse width shorter than that of the first laser pulse L1, preferably a short pulse length of about 1 nanosecond to about 1000 nanoseconds.

More preferably, the second laser pulse L2 has a pulse width of 5 ns to 50 ns. According to clinical tests, the best effect is obtained by the second pulse L2 having the pulse width of about 5 ns to 50 ns.

When the carbon lotion 20 that partially remains on the epidermis and the pore 8 is irradiated by the second laser pulse from the Q-switch of the Nd-YAG laser, the carbon lotion 20 absorbs the energy of the second laser pulse.

Since the second laser pulse has a very short pulse length, the time in which the carbon powders absorb the energy is short. As a result, the temperature of the carbon powders is abruptly raised.

The carbon powders with temperature abruptly raised are ruptured into small debris. If the carbon powders are burst in the pore 8, the stratum corneum S1 peeled off from the epidermis by the laser beam of the first laser pulse is completely removed therefrom.

Also, when the carbon powders are burst in the pore 8, old sebum 4, debris of keratin 6, and others, which are accumulated in the pore 8, are cleanly removed from the pore 8. As a result, passages of the pores clogged by sebum, bacteria, keratin, or the like are entirely opened.

Further, the second laser pulse L2 gives thermal stimulation to the inflammation around the pores to further accelerate the treatment of the inflammation.

After the stratum corneum S1 is removed from the epidermis by the radiation of the first laser pulse, the partially left stratum corneum S1 is entirely removed by the burst of the carbon lotion 20, thereby keeping the skin state clean and thus preventing development of the acne.

Figure 8:
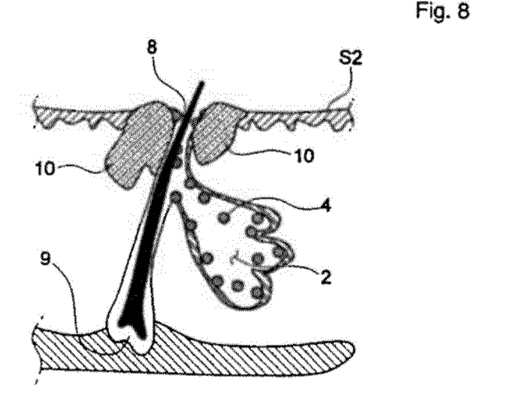
FIG. 8 illustrates an exemplary surround area of acne after first and second laser pulses are irradiated according to an embodiment.

FIG. 8 is a view illustrating the surrounding area of the acne after the first and second laser pulses are irradiated.

Referring to FIG. 8, the burst of the carbon powders by the irradiation of the second laser pulse having a short pulse width causes the pores to open, which can keep the pores clean, and restrains excessive secretion of the sebum gland, thereby curing the acne.

Preferably, the first laser pulse L1 and the second laser pulse L2 are adapted to have energy density of about 1.5 J/cm$^2$ to about 3.0 J/cm$^2$.

With the method of curing the inflammatory acne according to the present invention, the carbon lotion 20 is irradiated with the first laser pulse having a relatively long pulse length, so that the stratum corneum is separated from the epidermis so as to be easily removed from the epidermis, and an epidermal layer and a dermal layer are stimulated to activate generation or reorganization of cells such as collagen and thus further accelerate regeneration of the skin. Further, it sterilizes acne bacilli such as *Propionibacterium* acne to eliminate the inflammation 10. Then, the carbon powders are irradiated with the second laser pulse having a relatively short pulse length, so that the carbon powders are burst out to open the clogged pores and thus keep the pores clean, and to restrain the excessive secretion of the sebum gland and thus basically eliminate the onset causes of acne, thereby curing the acne.

In this embodiment the irradiation of the first laser pulse and second laser pulse is achieved by using the Nd:YAG laser having the Q-switch, but the present invention is not limited thereto. It is, of course, noted that the case of using a laser capable of oscillating a laser pulse of about 1 nanosecond to about 1000 nanoseconds after a laser pulse of about 1 microsecond to about 1000 microseconds is oscillated is within the scope of the present disclosure.

Figure 9:
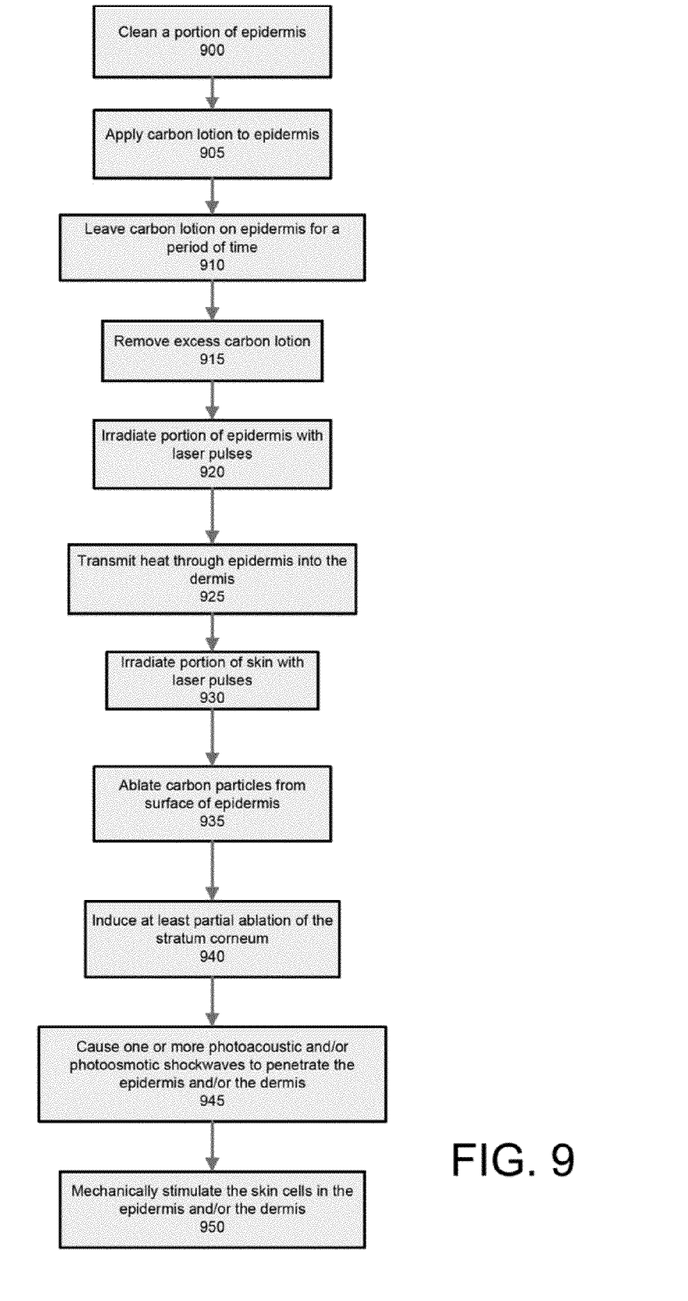
FIGS. 9-12 illustrate exemplary methods of treating skin according to an embodiment.

FIG. 9 illustrates a method of treating a portion of skin according to an embodiment. As illustrated by FIG. 9, a portion of epidermis to be treated may be cleaned 900. A carbon lotion may be evenly applied 905 to the portion of the epidermis and the pores. In an embodiment, the carbon lotion may be left 910 on the epidermis for a period of time to allow the carbon lotion to penetrate the pores of the epidermis. Excess carbon lotion may be removed 915.

In an embodiment, a portion of the epidermis to be treated may be irradiated 920 with one or more laser pulses. In an embodiment, the portion of the epidermis may be irradiated 920 with one or more laser pulses from a 1064 nm Nd:YAG laser. The laser pulses may have a pulse width of about 300 μs. The laser pulses may be irradiated 920 with minimal overlapping. In an embodiment, the laser pulses may be irradiated 920 in one pass over the portion of the epidermis to be treated. In an embodiment, application of the laser pulses may heat the tissue to which they are applied through nonablative absorption of the laser bean in the carbon lotion. The generated heat may be transmitted 925 through the epidermis into the dermis.

In an embodiment, one or more laser pulses from a laser operating in a Q-switched mode may be irradiated 930 onto the portion of the epidermis to be treated. For example, laser pulses from a 1064 nm Nd:YAG laser operating in Q-switched mode may be irradiated 930 onto the portion of the epidermis to be treated. In an embodiment, the pulse width of the laser pulses may be in a range of about 5 ns to about 7 ns. In an embodiment, application of a Q-switched mode laser pulse may ablate 935 the carbon particles from the treated portion of skin. In an embodiment, the ablated carbon particles may include those particles that have penetrated one or more enlarged pores of the treated epidermis. In an embodiment, irradiation 930 of the Q-switched mode laser pulses may induce 940 at least partial ablation of the stratum corneum, and may cause 945 one or more photoacoustic and/or photoosmotic shockwaves to penetrate the epidermis and dermis. These shockwaves may mechanically stimulate 950 the skin cells in the epidermis and/or the dermis.

In an embodiment, the method of treating a portion of skin described in FIG. 9 may be used to treat enlarged skin pores.

The nonablative heating effect in connection with the application of micropulsed energy to the carbon particles and epidermis and the ablation of the particles off of the epidermis may cause mild damage to the epidermis and controlled subablative heating of the dermis. In conjunction with the photomechanical stimulation described above, the body's natural wound repair mechanism may be triggered, and epidermal renewal and neocollagenesis may occur. Epidermal renewal and neocollagenesis may result in a decrease in the size of one or more enlarged pores in the epidermis through the combination of skin tightening and plumping of the dermis due to the dermal remodeling process.

In an embodiment, the method of treating a portion of skin described in FIG. 9 may be used to treat one or more indicators, effects or conditions of aging skin, such as photoaging and/or chronological-aging skin according to an embodiment. Photoaging skin may include skin that has damage due to prolonged exposure to ultraviolet radiation. Chronological-aging skin may be skin that has aged naturally over time. Exemplary effects or conditions of photoaging and/or chronological-aging skin may include, without limitation, lines, wrinkles, dark spots, freckling, leathery skin, enlarged pores with mild hyperkertosis, dull/lax epidermis and/or mild dyschromia.

In an embodiment, the treatment method described by FIG. 9 may induce inflammation followed by proliferation and remodeling of the treated portion of skin. This repair process may cause dermal neocollagenesis and epidermal renewal, which may produce a plumper, better-hydrated and younger-looking epidermis through a thinner and tighter stratum corenum and thermal and photomechanical stimulation of the epidermal basal layer keratinocytes. Normalization of hypermelanogenesic melanocytes may help remove mild dyschomic lesions.

Figure 10:
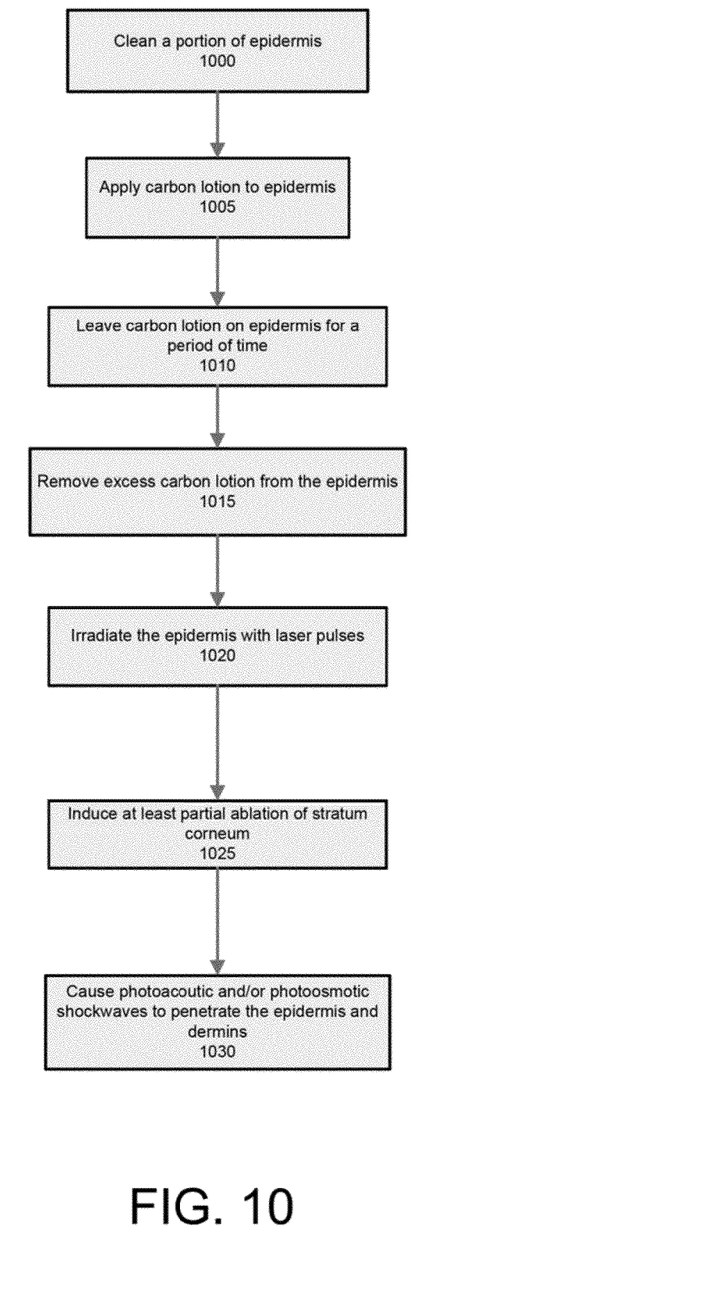

FIG. 10 illustrates an exemplary method of treating a portion of skin according to an embodiment. As illustrated by FIG. 10, a portion of epidermis to be treated may be cleaned 1000. A carbon lotion may be evenly applied 1005 to the portion of the epidermis. In an embodiment, the carbon lotion may be left 1010 on the epidermis for a period of time to allow the carbon lotion to evenly coat the surface of the stratum corneum and/or to penetrate the pores of the epidermis. Excess carbon lotion may be removed 1015.

In an embodiment, a portion of epidermis to be treated may be irradiated 1020 by one or more laser pulses. In an embodiment, a portion of epidermis to be treated may be irradiated 1020 by one or more pulses of a 1064 nm Nd:YAG laser operating in Q-switched mode. In an embodiment, the pulse width of the one or more laser pulses may be in a range of about 5 ns to about 50 ns. Application of the one or more laser pulses may remove the carbon particles in the carbon lotion from the skin portion through almost instantaneous ablation. In an embodiment, irradiation 1020 may induce 1025 at least partial ablation of the stratum corneum, and may cause 1030 one or more photoacoustic and/or photoosmotic shockwaves to penetrate the epidermis and dermis. These shockwaves may mechanically stimulate 1035 the skin cells in the epidermis and/or the dermis. The method of treating skin described in FIG. 10 may be used to treat acne, enlarged skin pores, photoaging skin and/or chronologically aging skin.

Figure 11:
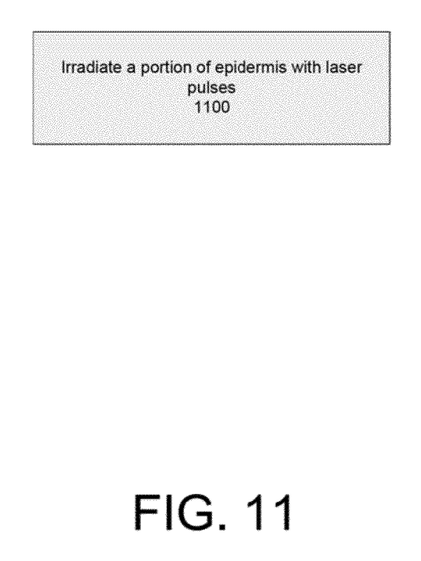

FIG. 11 illustrates an exemplary method of treating a portion of skin according to an embodiment. As illustrated by FIG. 11, one or more laser pulses may be irradiated 1100 onto the portion of the epidermis to be treated. In an embodiment, a portion of epidermis may be irradiated 1100 with one or more pulses of a 1064 nm Nd:YAG laser. The one or more laser pulses may have a pulse width in a range of about 5 ns to about 50 ns. The method of treating skin described in FIG. 11 may be used to treat acne, enlarged skin pores, photoaging skin and/or chronologically aging skin.

Figure 12:
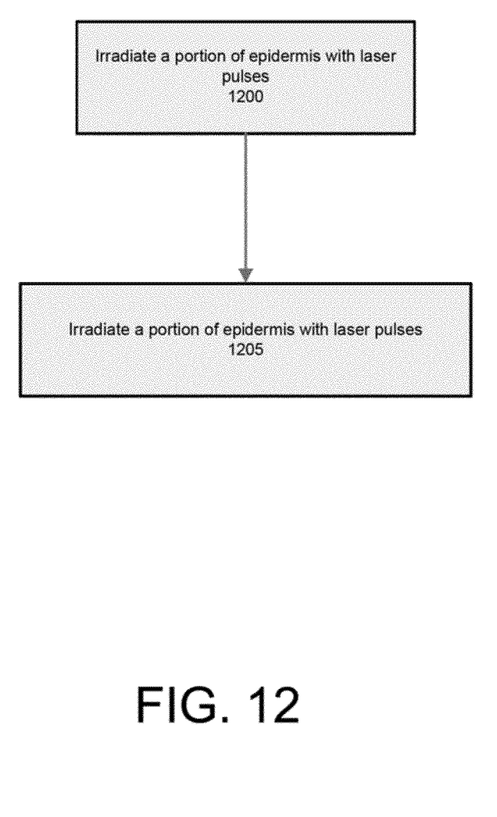

FIG. 12 illustrates an exemplary method of treating a portion of skin according to an embodiment. As illustrated by FIG. 12, one or more laser pulses may be irradiated 1200 onto the portion of the epidermis to be treated. In an embodiment, a portion of epidermis may be irradiated 1200 with one or more laser pulses from a 1064 nm Nd:YAG micropulsed laser having a pulse width of about 300 µs. In an embodiment, the treated portion of skin may be subsequently irradiated 1205 with one or more laser pulses of a 1064 nm Nd:YAG laser operating in Q-switched mode. In an embodiment, the laser pulses may have a pulse width in a range of about 5 ns to about 50 ns. In an embodiment, the method of treating skin described in FIG. 12 may be used to treat acne, enlarged skin pores, photoaging skin and/or chronologically aging skin.

The forgoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

As apparent from the above description, the method of curing the inflammatory acne by using the carbon lotion and the pulsed laser, according to the present invention, has the following effects.

1) The carbon lotion applied onto the epidermis is irradiated with the first laser pulse having a relatively long pulse length (i.e., about 1 microsecond to about 1000 microseconds) and the second laser pulse having a relatively short pulse length (i.e., about 1 nanosecond to about 1000 nanoseconds), in order to simply and effectively cure the inflammatory acne.

2) The carbon lotion applied onto the epidermis is irradiated with the first laser pulse having a relatively long pulse length (i.e., about 1 microsecond to about 1000 microseconds), so that the stratum corneum S1 is evenly eliminated by the heat generated from the carbon lotion, and the epidermal layer S2 and the dermal layer S3 are stimulated.

By stimulating the epidermal layer and the dermal layer, the generation or reorganization of cells such as collagen is activated, and thus the regeneration of the skin cells is further accelerated.

3) Through the uniform regeneration of the dermal cells, the wound is quickly closed, and it can prevent the scar due to the acne.

4) The carbon lotion applied onto the epidermis is irradiated with the second laser pulse having a relatively short pulse length (i.e., about 1 nanosecond to about 1000 nanoseconds), in order to burst out the carbon powders in the pore and thus eliminate the stratum corneum S1 and open the pore.

Through the opening of the pores, the old sebum, the debris of keratin, and others are cleanly removed from the pore 8, so that the passage of the pore 8 clogged by the sebum, the bacteria, the keratin, and others is completely opened.

Since the passage of the pore 8 is completely opened, the secretion of the sebum gland can be adjusted.

5) Since the carbon lotion applied onto the epidermis is irradiated with the first laser pulse having a relatively long pulse length (i.e., about 1 microsecond to about 1000 microseconds) and the second laser pulse having a relatively short pulse length (i.e., about 1 nanosecond to about 1000 nanoseconds), acne bacilli such as *Propionibacterium* acne are sterilized to eliminate the onset causes of acne.

6) According to the above effects, proper prognosis is obtained in the process of curing the acne.

What is claimed is:

1. A method of treating a portion of skin, the method comprising:
    applying a carbon lotion to a portion of skin
    irradiating the portion of skin with one or more first laser pulses, wherein each of the one or more first laser pulses has a first pulse width in a range of 100 μs to 1000 μs; and
    irradiating the portion of skin with one or more second laser pulses, wherein a laser producing the first and second laser pulses has an oscillation wavelength of 1064 nm, wherein each of the one or more second pulses has a second pulse width in a range of about 5 ns to about 50 ns.

2. The method of claim 1, wherein the laser comprises a pulsed Nd:YAG laser.

3. The method of claim 1, wherein each of the one or more first laser pulses has a pulse width of about 300 μs.

4. The method of claim 1, wherein irradiating the portion of skin with one or more first laser pulses comprises irradiating the portion of skin with one or more first laser pulses with minimal overlapping.

5. The method of claim 1, wherein irradiating the portion of skin with one or more first laser pulses comprises irradiating the portion of skin with one or more first laser pulses in a single pass over the portion of skin.

6. The method of claim 1, wherein irradiating the portion of skin with one or more second laser pulses comprises irradiating the portion of skin with one or more second laser pulses that are generated by the laser operating in a Q-switched mode.

7. The method of claim 6, wherein each of the one or more second laser pulses has a pulse width in a range of about 5 ns to about 7 ns.

8. The method of claim 1, wherein irradiating the portion of skin with one or more second laser pulses comprises:
    ablating one or more carbon particles from the carbon lotion that is within one or more enlarged pores in the portion of skin causing at least partial ablation of a stratum corenum of the portion of skin, and
    causing one or more photoacoustic or photoosmotic shockwaves to penetrate the portion of skin and stimulate one or more skin cells within the portion of skin.

9. A method of treating a portion of skin, the method comprising:
    applying a carbon lotion to a portion of skin comprising one or more indicators of aging;
    irradiating the portion of skin with one or more first laser pulses, wherein each of the one or more first laser pulses has a first pulse width in a range of 100 μs to 1000 μs; and
    irradiating the portion of skin with one or more second laser pulses, wherein a laser producing the first and second laser pulses has an oscillation wavelength of 1064 nm, wherein each of the one or more second pulses has a second pulse width in a range of about 5 ns to about 50 ns.

10. The method of claim 1, further comprising:
    prior to irradiating the portion of the skin with the one or more first laser pulses and the one or more second laser pulses, removing excess carbon lotion from the portion of skin.

11. The method of claim 1, further comprising:
    prior to irradiating the portion of the skin with the one or more first laser pulses and the one or more second laser pulses, removing excess carbon lotion from the portion of skin.

12. The method of claim 9, wherein the laser comprises a pulsed Nd:YAG laser.

13. The method of claim 9, wherein each of the one or more first laser pulses has a pulse width of about 300 μs.

14. The method of claim 9, wherein irradiating the portion of skin with one or more first laser pulses comprises irradiating the portion of skin with one or more first laser pulses with minimal overlapping.

15. The method of claim 9, wherein irradiating the portion of skin with one or more first laser pulses comprises irradiating the portion of skin with one or more first laser pulses in a single pass over the portion of skin.

16. The method of claim 9, wherein irradiating the portion of skin with one or more second laser pulses comprises irradiating the portion of skin with one or more second laser pulses that are generated by the laser operating in a Q-switched mode.

17. The method of claim 16, wherein each of the one or more second laser pulses has a pulse width in a range of about 5 ns to about 7 ns.

18. The method of claim 9, wherein the portion of skin comprises one or more indicators of photoaging skin.

19. The method of claim 9, wherein the portion of skin comprises one or more indicators of chronological-aging skin.

* * * * *